United States Patent
Nakagawa

(10) Patent No.: US 10,111,582 B2
(45) Date of Patent: Oct. 30, 2018

(54) IMAGE PROCESSING DEVICE AND METHOD TO IDENTIFY DISEASE IN AN OCULAR FUNDUS IMAGE

(71) Applicant: KOWA COMPANY, LTD., Nagoya-shi, Aichi (JP)

(72) Inventor: Toshiaki Nakagawa, Higashimurayama (JP)

(73) Assignee: KOWA COMPANY, LTD. (JP)

( * ) Notice: Subject to any disclaimer, the term of this patent is extended or adjusted under 35 U.S.C. 154(b) by 0 days.

(21) Appl. No.: 15/307,887

(22) PCT Filed: May 1, 2015

(86) PCT No.: PCT/JP2015/063054
§ 371 (c)(1),
(2) Date: Oct. 31, 2016

(87) PCT Pub. No.: WO2015/167005
PCT Pub. Date: Nov. 5, 2015

(65) Prior Publication Data
US 2017/0049314 A1    Feb. 23, 2017

(30) Foreign Application Priority Data
May 2, 2014    (JP) ................................ 2014-095299

(51) Int. Cl.
*G06K 9/00* (2006.01)
*A61B 3/00* (2006.01)
(Continued)

(52) U.S. Cl.
CPC .............. *A61B 3/0025* (2013.01); *A61B 3/10* (2013.01); *A61B 3/12* (2013.01); *G06T 7/0012* (2013.01);
(Continued)

(58) Field of Classification Search
CPC ........... A61B 3/0025; A61B 3/10; A61B 3/12; G06T 2207/10101; G06T 2207/30041; G06T 7/0012; G06T 7/0081
See application file for complete search history.

(56) References Cited

U.S. PATENT DOCUMENTS

| | | | |
|---|---|---|---|
| 5,116,116 A | 5/1992 | Aizu et al. | 351/221 |
| 5,594,807 A | 1/1997 | Liu | 382/128 |

(Continued)

FOREIGN PATENT DOCUMENTS

| | | |
|---|---|---|
| JP | 2232030 | 9/1990 |
| JP | 2004512538 | 4/2004 |

(Continued)

OTHER PUBLICATIONS

Kirk W. Gossage, et al., "Texture analysis of optical coherence tomography images: feasibility for tissue classification", Journal of Biomedical Optics, 2003. 07. vol. 8 No. 3, p. 570-p. 575.
(Continued)

*Primary Examiner* — Nirav G Patel
(74) *Attorney, Agent, or Firm* — Adams & Wilks

(57) ABSTRACT

An image processing device comprises an enhancement processing unit that enhances a speckle pattern in an ocular fundus tomographic image. A region-of-interest setting unit sets a desired region in the ocular fundus tomographic image with the enhanced speckle pattern as a region-of-interest, and a feature value extracting unit extracts a feature value of the speckle pattern in the region-of-interest. A disease determining unit makes disease determination for an ocular fundus on the basis of the feature value, and a mapping unit maps, in the ocular fundus tomographic image, a site of the ocular fundus that is determined to have a disease. An image processing method comprises enhancing a speckle pattern in an ocular fundus tomographic image; setting a desired region in the ocular fundus tomographic image with the
(Continued)

enhanced speckle pattern as a region-of-interest; extracting a feature value of the speckle pattern in the region-of-interest; and making disease determination for an ocular fundus on the basis of the feature value.

12 Claims, 6 Drawing Sheets

(51) Int. Cl.
*A61B 3/10* (2006.01)
*A61B 3/12* (2006.01)
*G06T 7/00* (2017.01)

(52) U.S. Cl.
CPC .. *G06T 7/0081* (2013.01); *G06T 2207/10101* (2013.01); *G06T 2207/30041* (2013.01)

(56) References Cited

U.S. PATENT DOCUMENTS

| | | | |
|---|---|---|---|
| 2002/0183601 A1 | 12/2002 | Tearney et al. | 600/310 |
| 2011/0013002 A1 | 1/2011 | Thompson et al. | 348/77 |
| 2012/0022338 A1 | 1/2012 | Subramaniam et al. | 600/301 |
| 2012/0113390 A1 | 5/2012 | Torii et al. | 351/208 |
| 2012/0150029 A1* | 6/2012 | Debuc | A61B 3/102 600/425 |
| 2013/0144137 A1 | 6/2013 | Zalevsky et al. | 600/314 |
| 2013/0195340 A1 | 8/2013 | Iwase et al. | 382/131 |
| 2013/0235342 A1 | 9/2013 | Makihira | 351/206 |
| 2014/0193095 A1* | 7/2014 | Choe | G06T 5/002 382/274 |

FOREIGN PATENT DOCUMENTS

| | | |
|---|---|---|
| JP | 2010532699 | 10/2010 |
| JP | 2011224410 | 11/2011 |
| JP | 2012100714 | 5/2012 |
| JP | 2013153884 | 8/2013 |
| JP | 2013530741 | 8/2013 |
| JP | 2013183909 | 9/2013 |

OTHER PUBLICATIONS

Andras A. Lindenmaier, et al., "Texture analysis of optical coherence tomography speckle for characterizing biological tissues in vivo", Optics Letters. Apr. 15, 2013, vol. 38, No. 8, p. 1280-p. 1282.
Mikhail Yu. Kirillin, et al., "Speckle statistics in OCT images: Monte Carlo simulations and experimental studies", Optics Letters, Jun. 15, 2014, vol. 39 No. 12, p. 3472-p. 3475.
International Search Report dated Jul. 28, 2015 in International Application No. PCT/JP2015/06304.
Xuan Liu et al., "Spectroscopic-speckle variance OCT for microvasculature detection and analysis", Journal of Biomedical Optics Express, Oct. 4, 2011, vol. 2 No. 11, p. 2995-p. 3009.
European Search Report dated Dec. 18, 2017 in Application No. 15 785 245.0.

* cited by examiner

IMAGE PROCESSING DEVICE AND METHOD TO IDENTIFY DISEASE IN AN OCULAR FUNDUS IMAGE

TECHNICAL FIELD

The present invention relates to an image processing device, image processing method and image processing program for processing tomographic images captured by a tomographic image capturing device or the like and generating an image suitable as a diagnostic image.

BACKGROUND ART

Tomographic image capturing devices are put into practical use as a type of ophthalmic diagnostic device. The tomographic image capturing devices capture tomographic images of ocular fundi utilizing optical interference of so-called OCT (Optical Coherence Tomography).

There is a technique of arithmetically averaging a plurality of images to improve the image quality of an ocular fundus image obtained by the OCT. When the image processing of arithmetically averaging a plurality of images is performed, a speckle pattern disappears. The speckle pattern as referred to herein is an image pattern based on a phenomenon that portions of high intensity and low intensity of scattered light occur due to an indefinitely large number of superpositions of scattered light from a scattering body in the object to be measured. This is a physical phenomenon similar to a so-called interference phenomenon and the speckle pattern itself does not directly represent the structure of an ocular fundus that is the object to be measured. In this context, Patent Literature 1 discloses a technique of regarding the speckle pattern as noises and combining tomographic images thereby to cause the speckle pattern to disappear, thus obtaining a high-quality tomographic image.

On the other hand, Patent Literature 2 discloses an ultrasonograph that obtains an ultrasonographic image in a subject under test on the basis of echo signals of ultrasonic waves. This ultrasonograph is provided with an analysis algorithm capable of observing a lesion by positively taking advantage of a speckle pattern appearing in the ultrasonographic image and utilizing its statistical properties to smooth an image of the speckle part and extract a microstructure. This literature also discloses a technique of utilizing a phenomenon that the probability density distribution of brightness values of echo signals reflected from a normal liver follows the Rayleigh distribution and comparing the variance values to determine whether the probability density distribution obtained by actual measurement follows the Rayleigh distribution as the theoretical figure.

Non-Patent Literature 1 discloses that the speckle pattern of OCT can be quantified in accordance with the gamma distribution.

PRIOR ART LITERATURE

Patent Literature

[Patent Literature 1] JP2013-183909A
[Patent Literature 2] JP2011-224410A

Non-Patent Literature

[Non-Patent Literature 1] Texture analysis of OCT speckle for characterizing biological tissues in vivo, Optics Letters, 38(8), 2013.

SUMMARY OF THE INVENTION

Problems to be Solved by the Invention

As described above, the speckle pattern itself does not directly represent the structure of an ocular fundus as the object to be measured, but is recognized to vary in the appearance in accordance with the state of ocular fundus. The present inventor has therefore focused attention on, rather than merely regarding the speckle pattern as noises, positively taking advantage of its statistical properties thereby to obtain more detailed information regarding the state of ocular fundus from the tomographic image of the ocular fundus.

In particular, as suggested in Non-Patent Literature 1, a feature value of the speckle pattern can be quantified for each image by utilizing the phenomenon that the speckle pattern follows the gamma distribution. Disease determination will thus be possible if more detailed information regarding the state of ocular fundus is obtained on the basis of data in which the feature value of the speckle pattern is quantified.

Therefore, objects of the present invention include providing an image processing device, image processing method and image processing program that utilize the speckle pattern in a positive manner thereby to obtain more detailed information regarding the state of ocular fundus tissues from the ocular fundus tomographic image and can perform disease determination for the ocular fundus, rather than owing to an idea of merely improving the image quality of the OCT ocular fundus tomographic image thereby to improve the visibility of the ocular fundus tomographic image as in the prior art.

Means for Solving the Problems

To achieve the above objects, according to a first aspect of the present invention, there is provided an image processing device comprising: an enhancement processing means configured to enhance a speckle pattern in an ocular fundus tomographic image; a region-of-interest setting means configured to set a desired region in the ocular fundus tomographic image with the enhanced speckle pattern as a region-of-interest; a feature value extracting means configured to extract a feature value of the speckle pattern in the region-of-interest; and a disease determining means configured to make disease determination for an ocular fundus on the basis of the feature value (Invention 1).

According to the above invention (Invention 1), detailed information regarding the state of ocular fundus tissues, which would not be completely perceived from the conventional OCT ocular fundus tomographic image, can be obtained by positively utilizing the speckle pattern in the ocular fundus tomographic image to perform the disease determination for the ocular fundus in each region-of-interest. The disease determination in the present invention refers to a concept including not only determining merely whether a disease of the ocular fundus is present or absent but also all possible determinations regarding a disease of the ocular fundus, such as determining the disease name, determining the stage of progression of the disease, and determining the degree of suspicion of the disease.

In the above invention (Invention 1), it is preferred that the region-of-interest is set within one retina layer of a retina layer structure displayed in the ocular fundus tomographic image (Invention 2).

According to the above invention (Invention 2), the region-of-interest is set within one retina layer so as not to be set across two or more retina layers, and the feature value analysis for the speckle pattern can thereby be individually executed for each region in the retina layer structure. Therefore, the accuracy of evaluation is improved, and more detailed information regarding the state of ocular fundus tissues can be obtained.

In the above invention (Invention 1, 2), it is preferred that the image processing device further comprises a mapping means configured to map, in the ocular fundus tomographic image, a site of the ocular fundus that is determined to have a disease by the disease determining means (Invention 3).

According to the above invention (Invention 3), the disease site is mapped in the ocular fundus tomographic image and thereby the result of disease determination can readily be perceived.

In the above invention (Invention 1 to 3), it is preferred that the enhancement processing means selects a plurality of ocular fundus tomographic images having similar speckle patterns from among a plurality of captured ocular fundus tomographic images and performs an arithmetic averaging process on the selected plurality of ocular fundus tomographic images having similar speckle patterns (Invention 4).

In the above invention (Invention 1 to 4), it is preferred that the feature value extracting means creates a histogram on the basis of brightness of the speckle pattern (Invention 5).

In the above invention (Invention 1 to 5), the disease determining means may compare the feature value of the speckle pattern with a reference feature value that is preliminarily acquired (Invention 6) or may also formulate the feature value of the speckle pattern into a mathematical formula and perform the disease determination on the basis of whether a parameter in the mathematical formula exceeds a predetermined threshold (Invention 7).

According to a second aspect of the present invention, there is provided an image processing method comprising: a step of enhancing a speckle pattern in an ocular fundus tomographic image; a step of setting a desired region in the ocular fundus tomographic image with the enhanced speckle pattern as a region-of-interest; a step of extracting a feature value of the speckle pattern in the region-of-interest; and a step of making disease determination for an ocular fundus on the basis of the feature value (Invention 8).

According to the above invention (Invention 8), detailed information regarding the state of ocular fundus tissues, which would not be completely perceived from the conventional OCT ocular fundus tomographic image, can be obtained by positively utilizing the speckle pattern in the ocular fundus tomographic image to perform the disease determination for the ocular fundus in each region-of-interest.

In the above invention (Invention 8), it is preferred that the region-of-interest is set within one retina layer of a retina layer structure displayed in the ocular fundus tomographic image (Invention 9).

According to the above invention (Invention 9), the region-of-interest is set within one retina layer so as not to be set across two or more retina layers, and the feature value analysis for the speckle pattern can thereby be individually executed for each region in the retina layer structure. Therefore, the accuracy of evaluation is improved, and more detailed information regarding the state of ocular fundus tissues can be obtained.

In the above invention (Invention 8, 9), it is preferred that the image processing method further comprises a step of mapping, in the ocular fundus tomographic image, a site of the ocular fundus that is determined to have a disease in the step of performing disease determination (Invention 10).

According to the above invention (Invention 10), the disease site is mapped in the ocular fundus tomographic image and thereby the result of disease determination can readily be perceived.

In the above invention (Invention 8 to 10), it is preferred that the step of enhancing a speckle pattern is a step of selecting a plurality of ocular fundus tomographic images having similar speckle patterns from among a plurality of captured ocular fundus tomographic images and performing an arithmetic averaging process on the selected plurality of ocular fundus tomographic images having similar speckle patterns (Invention 11).

In the above invention (Invention 8 to 11), it is preferred that the step of extracting a feature value is a step of creating a histogram on the basis of brightness of the speckle pattern (Invention 12).

In the above invention (Invention 8 to 12), the step of performing disease determination may be a step of comparing the feature value of the speckle pattern with a reference feature value that is preliminarily acquired (Invention 13) or may also be a step of formulating the feature value of the speckle pattern into a mathematical formula and performing the disease determination on the basis of whether a parameter in the mathematical formula exceeds a predetermined threshold (Invention 14).

According to a third aspect of the present invention, there is provided an image processing program that is characterized by causing a computer to execute the image processing method as described in any one of Invention 8 to 14 (Invention 15).

According to the above invention (Invention 15), detailed information regarding the state of ocular fundus tissues, which would not be completely perceived from the conventional OCT ocular fundus tomographic image, can be obtained by positively utilizing the speckle pattern in the ocular fundus tomographic image to perform the disease determination for the ocular fundus in each region-of-interest.

Advantageous Effect of the Invention

According to the image processing device, image processing method and image processing program of the present invention, it is possible to utilize the speckle pattern in a positive manner thereby to obtain more detailed information regarding the state of ocular fundus tissues from the ocular fundus tomographic image and perform disease determination for the ocular fundus.

EMBODIMENTS FOR CARRYING OUT THE INVENTION

Hereinafter, embodiments of the present invention will be described in detail with reference to the drawings.

Figure 1:
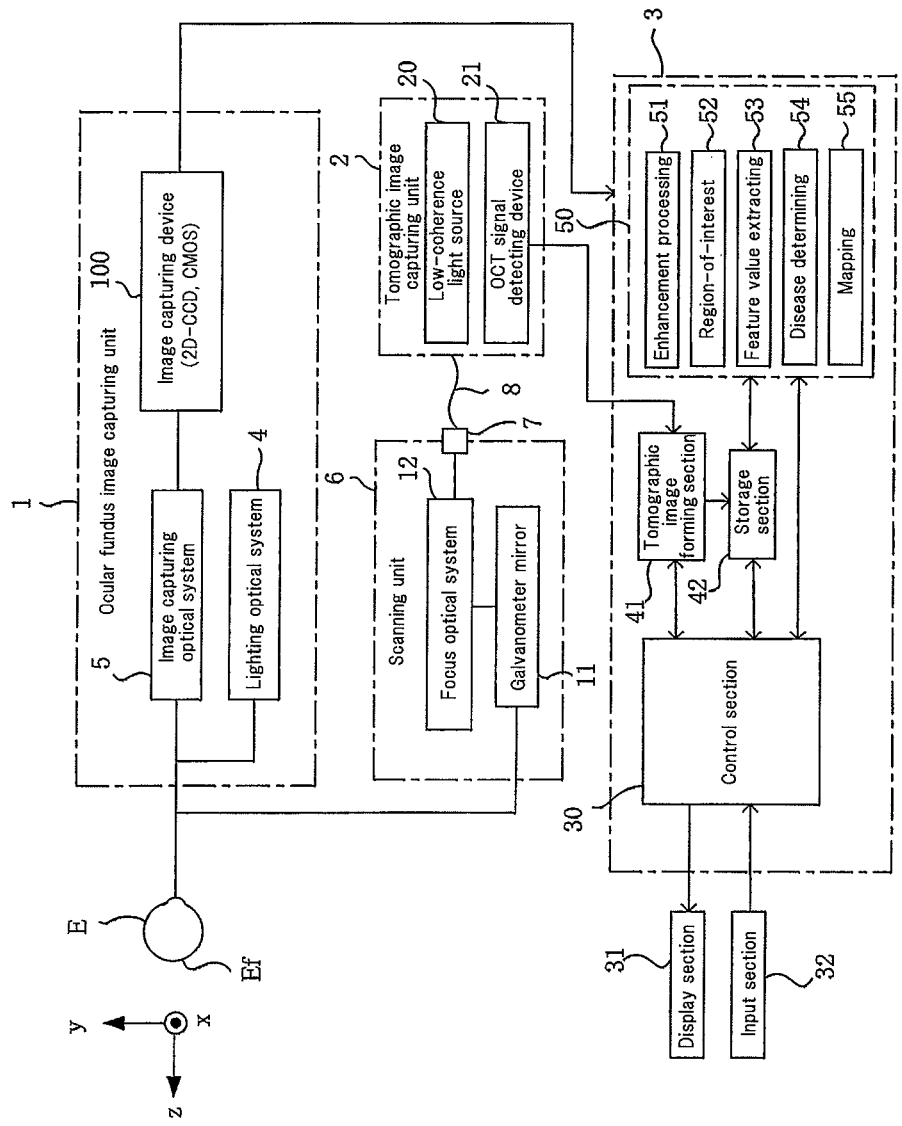
FIG. 1 is a schematic view illustrating an image processing system according to an embodiment of the present invention.

FIG. 1 is a schematic view illustrating the whole set of an image processing system according to an embodiment of the present invention, that is, a system that acquires tomographic images of the ocular fundus of a subject's eye to perform image processing. What is denoted by reference numeral 1 is an ocular fundus image capturing unit 1 for observation and image capturing of an ocular fundus (retina) Ef of a subject's eye E. The ocular fundus image capturing unit 1 may comprise a lighting optical system 4, an image capturing optical system 5, and an image capturing device 100 that is composed, for example, of a two-dimensional CCD or CMOS.

The lighting optical system 4 may comprise an observation light source such as a halogen lamp and an image capturing light source such as a xenon lamp, and the light from these light sources is introduced to the ocular fundus Ef via the lighting optical system 4 to light the ocular fundus Ef. The image capturing optical system 5 may comprise an optical system that includes necessary components, such as an objective lens, image capturing lens and focusing lens, and introduces the image capturing light reflected by the ocular fundus Ef to the image capturing device 100 along an image capturing optical path to capture images of the ocular fundus Ef.

Scanning unit 6 can introduce signal light (described later) reflected by the ocular fundus Ef to a tomographic image capturing unit 2. The scanning unit 6 may be a mechanism that comprises a known galvanometer mirror 11 for scanning the light from a low-coherence light source 20 of the tomographic image capturing unit 2 in the x-direction (horizontal direction) and y-direction (vertical direction), a focus optical system 12, and other necessary components.

The scanning unit 6 is optically connected via a connector 7 and a connecting line 8 to the tomographic image capturing unit 2 which captures tomographic images of the ocular fundus Ef.

Figure 2:
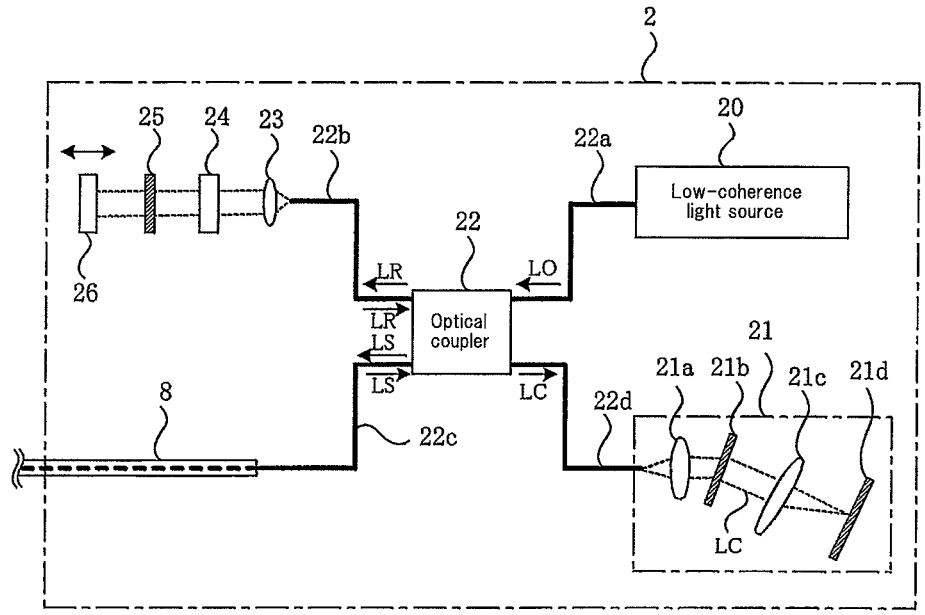
FIG. 2 is an optics view illustrating the detailed configuration of a tomographic image capturing unit according to the embodiment.

The tomographic image capturing unit 2 may be a known one that operates using the Fourier domain scheme (spectral domain method), for example, and the detailed configuration is illustrated in FIG. 2. The tomographic image capturing unit 2 may have a low-coherence light source 20 that emits light of a temporal coherence length of about several micrometers to several tens of micrometers at a wavelength of 700 nm to 1,100 nm.

The low coherence light LO generated by the low-coherence light source 20 is introduced into an optical coupler 22 through an optical fiber 22a and divided into reference light LR and signal light LS. The reference light LR passes through an optical fiber 22b, a collimator lens 23, a glass block 24, and a density filter 25 and reaches a reference mirror 26 that is movable in the optical axis direction for matching the optical path lengths. The glass block 24 and the density filter 25 can function as a delay means for matching the optical path lengths (optical distances) of the reference light LR and signal light LS and can also function as a means for matching the dispersion characteristics of the reference light LR and signal light LS.

The signal light LS passes through an optical fiber 22c inserted in the connecting line 8, reaches the ocular fundus Ef via the scanning unit 6 of FIG. 1, and scans the ocular fundus in the horizontal direction (x-direction) and the vertical direction (y-direction). The signal light LS reaching the ocular fundus Ef is reflected at the ocular fundus Ef and tracks back the above path to return to the optical coupler 22.

The reference light LR reflected from the reference mirror 26 and the signal light LS reflected from the ocular fundus Ef are superimposed by the optical coupler 22 to be interfering light LC. The interfering light LC is introduced into an OCT signal detecting device 21 via an optical fiber 22d. In the OCT signal detecting device 21, the interfering light LC is caused to be a parallel light flux by a collimator lens 21a, and the parallel light flux is then incident to a diffraction grating 21b to be diffracted and forms an image on a CCD 21d by an imaging lens 21c. The OCT signal detecting device 21 can generate an OCT signal that represents information regarding the depth direction (z-direction) of the ocular fundus by the diffracted interfering light.

The image processing system according to the present embodiment may be provided with an image processing device 3 that is composed, for example, of a personal computer connected to the tomographic image capturing unit 2 and other necessary components. The image processing device 3 may be provided with a control section 30 that is composed of a CPU, a RAM, a ROM, and other necessary components. The control section 30 can execute an image processing program to control the image processing as a whole.

Display section 31 may be composed, for example, of a display device such as an LCD. The display section 31 can display images, such as tomographic images and a front image, which are generated or processed in the image processing device 3, and associated information such as information regarding the subject, etc.

Input section 32 is for an input operation to the images displayed on the display section 31, using an input means such as a mouse, keyboard and input pen. An operator can use the input section 32 to provide commands to the image processing device 3, etc.

The image processing device 3 may be provided with a tomographic image forming section 41. The tomographic image forming section 41 may be realized as a dedicated electronic circuit that executes a known analyzing method such as the Fourier domain method (spectral domain method) or realized using an image processing program that is executed by the previously-described CPU, and forms tomographic images of the ocular fundus Ef on the basis of the OCT signal detected by the OCT signal detecting device 21. The tomographic images formed by the tomographic image forming section 41 may be stored in a storage section 42 that is composed, for example, of a semiconductor memory, hard disk or the like. The storage section 42 may further store the above-described image processing program and other necessary programs and data.

The image processing device 3 may be provided with an image processing section 50, which has an enhancement processing means 51, a region-of-interest setting means 52, a feature value extracting means 53, a disease determining means 54, and a mapping means 55.

The enhancement processing means 51 enhances a speckle pattern in each tomographic image formed by the tomographic image forming section 41. In the tomographic image formed by the tomographic image forming section 41, mere noises and a speckle pattern coexist and it is difficult to distinguish the noises and the speckle on the tomographic image. In order to obtain more detailed information regarding the state of ocular fundus tissues from the ocular fundus tomographic image by utilizing the speckle pattern in a positive manner, in the present embodiment, noises are removed as much as possible thereby to perform a process of enhancing the speckle pattern.

The region-of-interest setting means 52 sets, as a region-of-interest, a desired region in each tomographic image of which the speckle pattern is enhanced by the enhancement processing means 51. The region-of-interest is generally a region from which an operator wants to obtain more detailed information regarding the state of the ocular fundus, but is not limited thereto, provided that the region is a closed region in the ocular fundus tissues appearing in the tomographic image. Since the ocular fundus tissues are in a layered structure, the region-of-interest may be set within one retina layer of the retina layer structure of the ocular fundus displayed in the tomographic image and may not be set across two or more retina layers.

The feature value extracting means 53 extracts a feature value of the speckle pattern in the region-of-interest which is set by the region-of-interest setting means 52. The disease determining means 54 makes disease determination for the ocular fundus on the basis of the feature value which is extracted by the feature value extracting means 53. Examples of the disease determination for the ocular fundus include, for example, determining whether a disease of the ocular fundus is present or absent, determining the disease name, determining the stage of progression of the disease, and determining the degree of suspicion of the disease. The mapping means 55 may map, in the ocular fundus tomographic image, a site of the ocular fundus that is determined to have a disease by the disease determining means 54.

Figure 3:
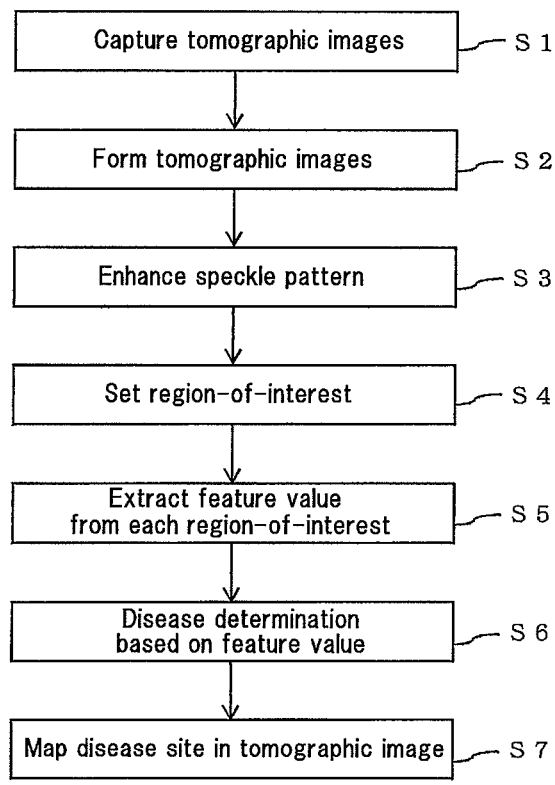
FIG. 3 is a flowchart illustrating the flow of image processing according to the embodiment.

Next, the image processing in the present embodiment will be described with reference to the flowchart illustrated in FIG. 3. This image processing may be performed by the control section 30 reading out the image processing program stored in the storage section 42 to execute it.

Figure 4:
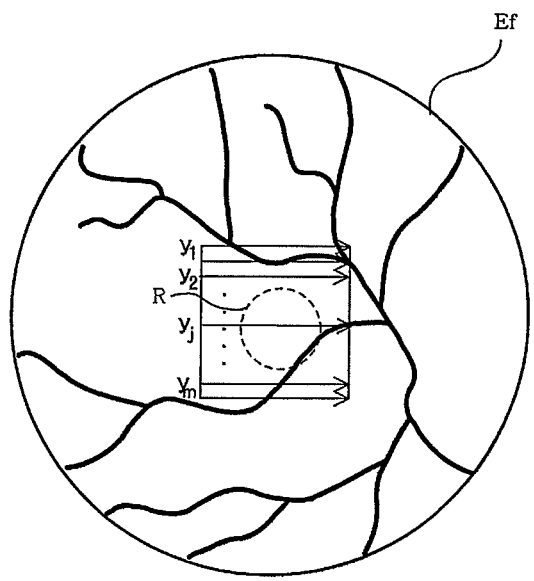
FIG. 4 is an explanatory view illustrating a state of scanning an ocular fundus with signal light in the embodiment.

First, prior to the image capturing of the tomographic images performed in step S1, the subject's eye E and the ocular fundus image capturing unit 1 are aligned and the ocular fundus Ef is caused to come into focus. In this state, the low-coherence light source 20 is turned on and the scanning unit 6 sweeps the signal light from the tomographic image capturing unit 2 in the x-direction and y-direction to scan the ocular fundus Ef. This state is illustrated in FIG. 4. Region R in which a macular region of the retina exists may be scanned in a direction parallel to the x-axis with n scanning lines $y_1, y_2, \ldots, y_n$.

The signal light LS reflected from the ocular fundus Ef is superimposed in the tomographic image capturing unit 2 with the reference light LR reflected from the reference mirror 26. This superimposition generates the interfering light LC and the OCT signal detecting device 21 generates the OCT signal. The tomographic image forming section 41 forms the tomographic images of the ocular fundus Ef on the basis of the OCT signal (step S2) and the formed tomographic images are stored in the storage section 42.

Figure 5:
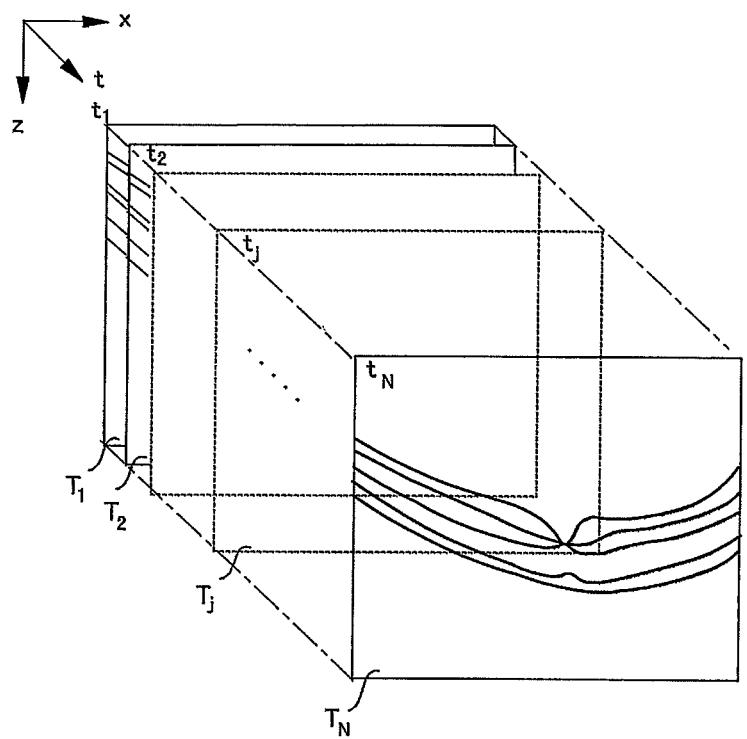
FIG. 5 is an explanatory view illustrating a state of acquiring a plurality of tomographic images in the embodiment.

FIG. 5 illustrates tomographic images $T_i$ (i=1 to N) each at different time $t_i$ (i=1 to N) of an xz-tomographic image (B-scan image) obtained by the scanning line $y_j$ passing through approximately the center of the macular region of the retina. The time interval between $t_i$ and $t_{i+1}$ corresponds to a time required for the next scanning line $y_{i+1}$ to start. These tomographic images $T_i$ (1=1 to N) may be formed every time $t_i$ (i=1 to N) in the tomographic image forming section 41 and stored sequentially in the storage section 42.

In each of the tomographic images stored sequentially in the storage section 42, a speckle pattern SP may appear together with other noises. In the present embodiment, an arithmetic averaging process may be performed on a plurality of the tomographic images to remove the noises as much as possible and enhance only the speckle pattern SP thereby to improve the image quality of a tomographic image.

Figure 6:
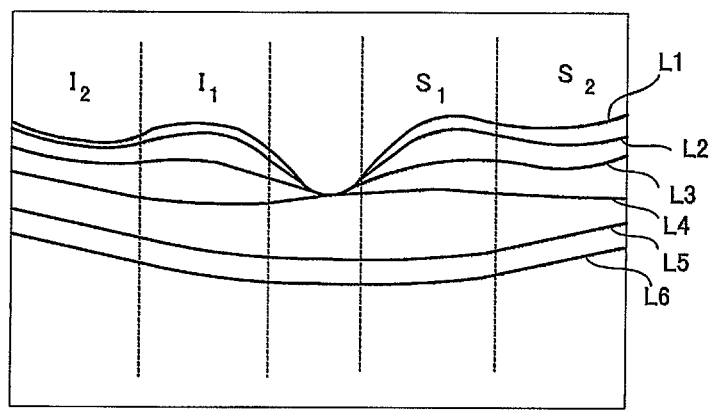
FIG. 6 is an explanatory view illustrating an arithmetically averaged image created in the embodiment.

In the present embodiment, 100 images of the tomographic images $T_i$ (i=1 to N) may be formed in the same site at different times (i.e. N=100) and stored in the storage section 42. Then, in step S3, the enhancement processing means 51 enhances the speckle pattern SP. Specifically, the enhancement processing means 51 may select 10 images of tomographic images having similar speckle patterns SP from among the 100 images of the tomographic images $T_i$ (i=1 to N), read out the 10 images of the tomographic images from the storage section 42, and perform arithmetic averaging on each pixel to create an arithmetically averaged image $T_a$. The speckle pattern SP does not disappear after the arithmetic averaging because the speckle pattern SP is similar in the selected 10 images of tomographic images, but the noises other than the speckle pattern SP disappear by the arithmetic averaging. Therefore, the arithmetically averaged image $T_a$ has improved image quality as a whole and the speckle pattern SP can easily be recognized. The arithmetically averaged image $T_a$ thus created may be stored in the storage section 42. FIG. 6 is an explanatory view illustrating the created arithmetically averaged image $T_a$. In the arithmetically averaged image $T_a$, L1 to L6 represent boundaries between layers in a retina layer structure. For descriptive purposes, the image is divided into four regions I1, I2, S1, and S2.

Figure 7:
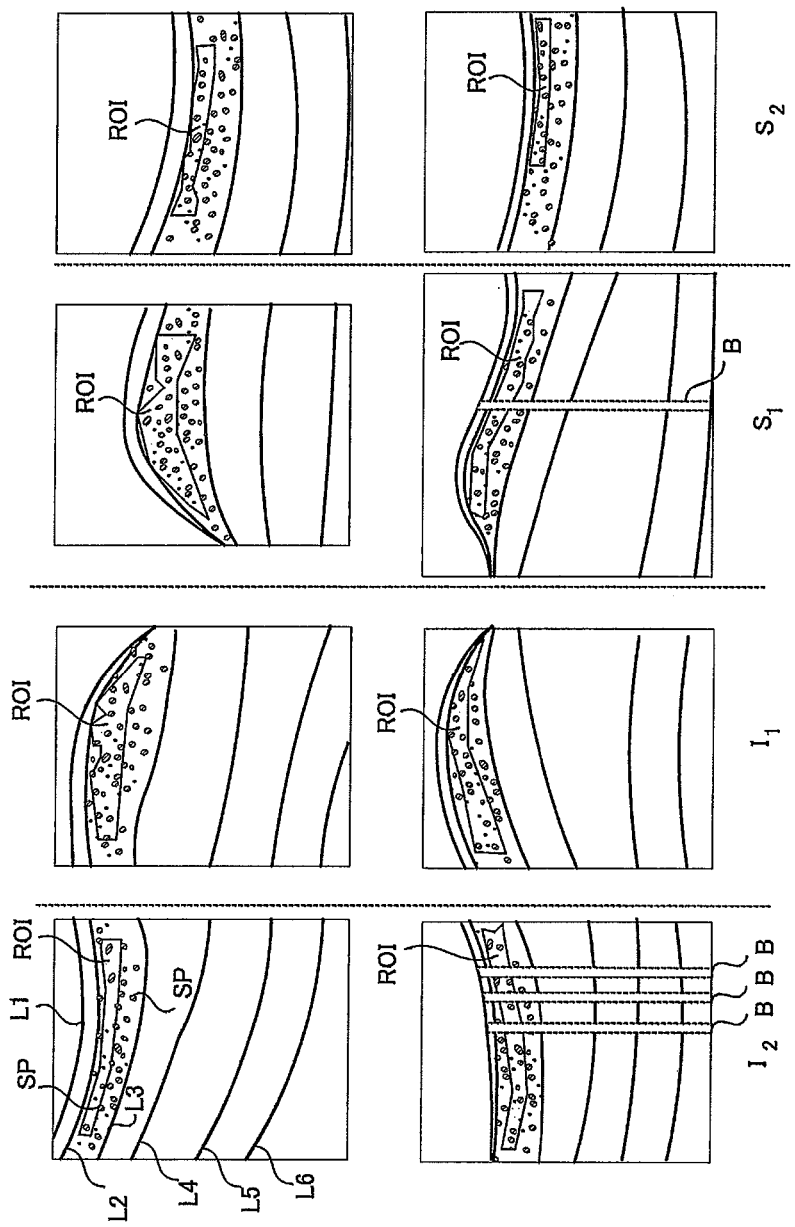
FIG. 7 is a set of explanatory views each illustrating an example of setting a region-of-interest in the embodiment.

Subsequently, in step S4, the region-of-interest setting means 52 performs setting of a region-of-interest ROI for the arithmetically averaged image $T_a$. Specifically, the region-of-interest ROI may be set, as illustrated in FIG. 7, within one retina layer of the retina layer structure of the ocular fundus displayed in the arithmetically averaged image $T_a$. The region-of-interest ROI may not be set across two or more retina layers and may be set so as to avoid blood vessels B in the retina layer structure. By setting the region-of-interest ROI in such a manner, the feature value analysis for the speckle pattern SP can be individually executed for each region in the retina layer structure. Therefore, the accuracy of evaluation is improved, and more detailed information regarding the state of ocular fundus tissues can be obtained.

Figure 8:
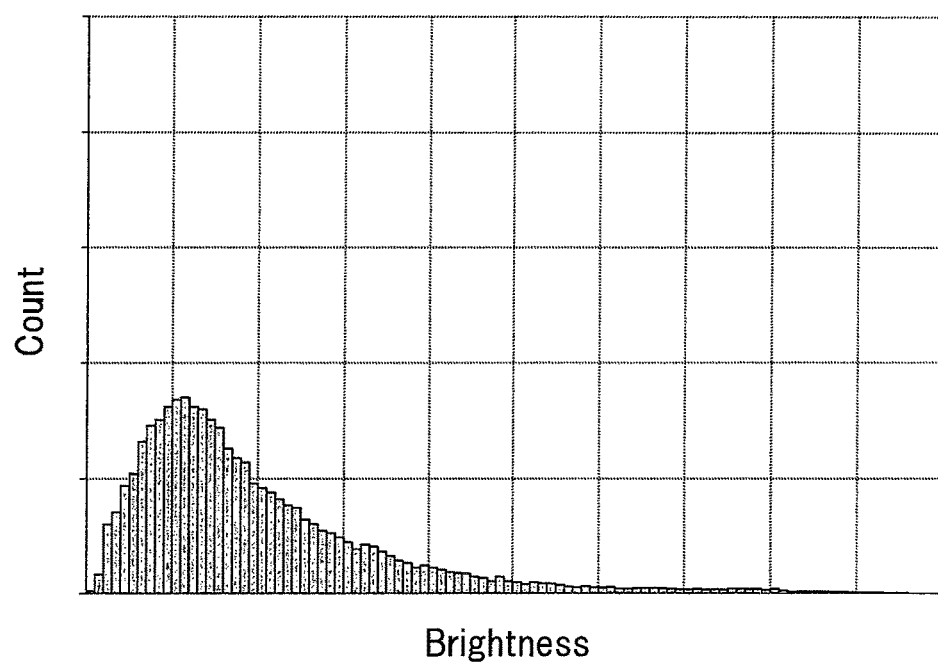
FIG. 8 is a histogram created in the embodiment.

After the region-of-interest ROI is set, the feature value extracting means 53 extracts a feature value of the speckle pattern SP in each region-of-interest ROI in step S5. Specifically, the feature value of the speckle pattern SP in the region-of-interest ROI may be extracted in the following manner. First, the signal intensity is measured for each pixel in the region-of-interest ROI, and the image in the region-of-interest ROI is digitized by performing an imaging process of 256-gradation in accordance with the signal intensity. This digitized image data is used as the basis to create a histogram as illustrated in FIG. 8, in which the horizontal axis represents the brightness and the vertical axis represents the count of pixels. Here, the knowledge is utilized that the speckle pattern of OCT can be quantified in accordance with the gamma distribution, and the gamma distribution function represented by Expression 1 is applied to that histogram using nonlinear regression analysis.

$$f(x, \alpha, \beta) = \frac{1}{\Gamma(\alpha)} \beta^{\alpha} x^{\alpha-1} e^{-\beta x} \quad \text{[Expression 1]}$$

In Expression 1, a is a shape parameter and β is a scale parameter. The gamma distribution function is applied by giving initial values of a and 3 and searching for optimum values by repetitive operation. The feature value of the speckle pattern SP in the region-of-interest ROI can be represented by those two parameters and, in particular, the ratio α/β may be representative of the feature value of the speckle pattern SP in the region-of-interest ROI.

After the feature value of the speckle pattern SP in the region-of-interest ROI is extracted, the disease determining means 54 determines, in step S6, presence or absence of a disease in the region-of-interest ROI on the basis of the feature value. Specifically, for making the disease determination, the storage section 42 may preliminarily store reference feature value data that represents the states of various ocular fundus tissues. For example, the above process of steps S3 to S5 may be preliminarily performed to extract the feature values of speckle patterns from the tomographic images of ocular fundi of normal eyes and abnormal eyes having a disease, and a reference feature value database may be provided such that the feature values are stored in the storage section 42 as reference feature value data that is associated with the state of an ocular fundus. Then, the feature value of the speckle pattern SP extracted in step S5 may be checked up with the feature value data of the reference feature value database to pick up reference feature value data that matches or approximates the feature value on the basis of the difference therebetween, and the state of ocular fundus tissues, such as the presence or absence of a disease and the stage of progression of the disease in the region-of-interest ROI, can be determined from the picked-up reference feature value data.

In an alternative embodiment, the disease determination in step S6 may be performed as below. For example, many tomographic images of ocular fundi of normal eyes and abnormal eyes having a disease may be prepared, the above process of steps S3 to S5 may be preliminarily performed to extract the feature values of speckle patterns from these tomographic images, and the relationship between the presence or absence of a disease and the parameters α and β or the relationship between the presence or absence of a disease and the ratio of α/β may be accumulated. Further, analysis may be performed as to which value when the parameters α and β or the ratio of α/β exceeds, a disease is recognized in the region-of-interest ROI, and a threshold to be used for the disease determination may be determined. Then, the state of ocular fundus tissues, such as the presence or absence of a disease and the stage of progression of the disease in the region-of-interest ROI, may be determined in accordance with whether the feature value of the speckle pattern extracted in step S5 exceeds the threshold.

Subsequently, in step S7, the mapping means 55 may map the site of the ocular fundus which is determined to have a disease, in the arithmetically averaged image $T_a$. When the disease site is mapped in the ocular fundus tomographic image and displayed, for example, by the display section 31, the result of disease determination can readily be perceived.

As will be understood, if the disease site is mapped with color in the ocular fundus tomographic image, the result can more readily be perceived.

When the image processing is performed in the above manner, the speckle pattern can be utilized in a positive manner thereby to obtain more detailed information regarding the state of ocular fundus tissues from the ocular fundus tomographic image, and the disease determination for the ocular fundus can be performed.

The image processing system according to the present invention has been heretofore described with reference to the drawings, but the present invention is not limited to the above embodiments and various modified embodiments can be carried out.

DESCRIPTION OF REFERENCE NUMERALS

1 Ocular fundus image capturing unit
2 Tomographic image capturing unit
3 Image processing device
4 Lighting optical system
5 Image capturing optical system
6 Scanning unit
20 Low-coherence light source
21 OCT signal detecting device
30 Control section
31 Display section
32 Input section
41 Tomographic image forming section
42 Storage section
50 Image processing section
51 Enhancement processing means
52 Region-of-interest setting means
53 Feature value extracting means
54 Disease determining means
55 Mapping means
100 Image capturing device

The invention claimed is:

1. An image processing device comprising:
enhancement processing means configured to enhance a speckle pattern in an ocular fundus tomographic image;
region-of-interest setting means configured to set a desired region in the ocular fundus tomographic image with the enhanced speckle pattern as a region-of-interest;
feature value extracting means configured to extract a feature value of the speckle pattern in the region-of-interest; and
disease determining means configured to make disease determination for an ocular fundus on a basis of the feature value; and
mapping means configured to map, in the ocular fundus tomographic image, a site of the ocular fundus that is determined to have a disease by the disease determining means.

2. The image processing device as recited in claim 1, wherein the region-of-interest is set within one retina layer of a retina layer structure displayed in the ocular fundus tomographic image.

3. The image processing device as recited in claim 1, wherein the enhancement processing means selects a plurality of ocular fundus tomographic images having similar speckle patterns from among a plurality of captured ocular fundus tomographic images and performs an arithmetic averaging process on the selected plurality of ocular fundus tomographic images having similar speckle patterns.

4. The image processing device as recited in claim 1, wherein the feature value extracting means creates a histogram on a basis of brightness of the speckle pattern.

5. The image processing device as recited in claim 1, wherein the disease determining means compares the feature value of the speckle pattern with a reference feature value that is preliminarily acquired.

6. The image processing device as recited in claim 1, wherein the disease determining means formulates the feature value of the speckle pattern into a mathematical formula and performs the disease determination on a basis of whether a parameter in the mathematical formula exceeds a predetermined threshold.

7. An image processing method comprising:
a step of enhancing a speckle pattern in an ocular fundus tomographic image;
a step of setting a desired region in the ocular fundus tomographic image with the enhanced speckle pattern as a region-of-interest;
a step of extracting a feature value of the speckle pattern in the region-of-interest,
a step of making disease determination for an ocular fundus on a basis of the feature value; and
a step of mapping, in the ocular fundus tomographic image, a site of the ocular fundus that is determined to have a disease in the step of performing disease determination.

8. The image processing method as recited in claim 7, wherein the region-of-interest is set within one retina layer of a retina layer structure displayed in the ocular fundus tomographic image.

9. The image processing method as recited in claim 7, wherein the step of enhancing a speckle pattern includes selecting a plurality of ocular fundus tomographic images having similar speckle patterns from among a plurality of captured ocular fundus tomographic images and performing an arithmetic averaging process on the selected plurality of ocular fundus tomographic images having similar speckle patterns.

10. The image processing method as recited in claim 7, wherein the step of extracting a feature value includes creating a histogram on a basis of brightness of the speckle pattern.

11. The image processing method as recited in claim 7, wherein the step of performing disease determination includes comparing the feature value of the speckle pattern with a reference feature value that is preliminarily acquired.

12. The image processing method as recited in claim 7, wherein the step of performing disease determination includes formulating the feature value of the speckle pattern into a mathematical formula and performing the disease determination on a basis of whether a parameter in the mathematical formula exceeds a predetermined threshold.

* * * * *